US 11,109,927 B2

(12) United States Patent
Kokubo et al.

(10) Patent No.: US 11,109,927 B2
(45) Date of Patent: Sep. 7, 2021

(54) JOINT DRIVING ACTUATOR AND MEDICAL SYSTEM

(71) Applicant: Sony Corporation, Tokyo (JP)

(72) Inventors: Wataru Kokubo, Tokyo (JP); Tetsuharu Fukushima, Tokyo (JP); Toshimitsu Tsuboi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 253 days.

(21) Appl. No.: 16/343,787

(22) PCT Filed: Oct. 13, 2017

(86) PCT No.: PCT/JP2017/037110
§ 371 (c)(1),
(2) Date: Apr. 22, 2019

(87) PCT Pub. No.: WO2018/088113
PCT Pub. Date: May 17, 2018

(65) Prior Publication Data
US 2019/0262090 A1 Aug. 29, 2019

(30) Foreign Application Priority Data
Nov. 10, 2016 (JP) .............................. JP2016-219522

(51) Int. Cl.
*A61B 34/00* (2016.01)
*A61B 90/25* (2016.01)
(Continued)

(52) U.S. Cl.
CPC ................ *A61B 34/70* (2016.02); *A61B 1/00* (2013.01); *A61B 1/00064* (2013.01);
(Continued)

(58) Field of Classification Search
CPC ............ A61B 1/00133; A61B 1/00149; A61B 1/0016; A61B 2034/2059;
(Continued)

(56) References Cited

U.S. PATENT DOCUMENTS 7,892,243 B2 * 2/2011 Stuart .................... A61B 34/77
606/130
8,275,443 B2 * 9/2012 Goldenberg ........... A61B 34/37
600/411
(Continued)

FOREIGN PATENT DOCUMENTS

JP     2002-307336 A     10/2002
JP     2010-524634 A     7/2010
(Continued)

OTHER PUBLICATIONS

International Search Report and Written Opinion dated Dec. 19, 2017 for PCT/JP2017/037110 filed on Oct. 13, 2017, 13 pages (including English Translation of International Search Report).

*Primary Examiner* — Ryan J. Severson
(74) *Attorney, Agent, or Firm* — Xsensus LLP

(57) ABSTRACT

A joint driving actuator that includes an ultrasonic motor that generates driving force for driving a joint, the ultrasonic motor including a stator fixed to a side of one arm that relatively rotates in the joint and a rotor fixed to a side of another arm that relatively rotates in the joint, the stator including a piezoelectric element that generates ultrasonic vibration, a torque sensor that detects external force applied to the joint, and an encoder that detects a rotational angle of the ultrasonic motor, the encoder being mounted on the one arm, the stator being fixed on the side thereof, and the torque sensor being mounted on the another arm, the rotor being fixed on the side thereof.

12 Claims, 7 Drawing Sheets

(51) Int. Cl.
  *B25J 19/00* (2006.01)
  *A61B 1/00* (2006.01)
(52) U.S. Cl.
  CPC .......... *A61B 1/00133* (2013.01); *A61B 90/25* (2016.02); *B25J 19/00* (2013.01)
(58) Field of Classification Search
  CPC ........ A61B 2090/065; A61B 2090/066; A61B 2090/067; A61B 2090/0811; A61B 2562/0261; A61B 34/70; A61B 34/74; A61B 90/25; A61B 90/50; B25J 19/00
  See application file for complete search history.

(56) References Cited

U.S. PATENT DOCUMENTS

| | | | | |
|---|---|---|---|---|
| 8,280,485 | B2* | 10/2012 | Goldenberg | A61B 34/30 600/411 |
| 8,397,624 | B2* | 3/2013 | Asai | F15B 15/02 91/500 |
| 8,683,884 | B2* | 4/2014 | Asai | F16H 25/18 74/89 |
| 10,335,959 | B2* | 7/2019 | Ogata | B25J 9/126 |
| 10,369,700 | B2* | 8/2019 | Kuroda | B25J 9/1651 |
| 2007/0250078 | A1* | 10/2007 | Stuart | A61B 34/76 606/130 |
| 2009/0326364 | A1* | 12/2009 | Goldenberg | A61B 34/37 600/411 |
| 2009/0326365 | A1* | 12/2009 | Goldenberg | A61B 34/30 600/411 |
| 2010/0170241 | A1* | 7/2010 | Asai | F15B 11/186 60/484 |
| 2011/0209570 | A1* | 9/2011 | Asai | F16H 25/18 74/25 |
| 2016/0263749 | A1* | 9/2016 | Ogata | B25J 17/00 |
| 2017/0080574 | A1* | 3/2017 | Kuroda | H04N 5/2257 |
| 2019/0262090 | A1* | 8/2019 | Kokubo | B25J 19/00 |

FOREIGN PATENT DOCUMENTS

| | | |
|---|---|---|
| JP | 4715863 B2 | 7/2011 |
| WO | 2009/152613 A1 | 12/2009 |
| WO | 2015/146850 A1 | 10/2015 |
| WO | 2016/006545 A1 | 1/2016 |
| WO | 2017/169118 A1 | 10/2017 |

* cited by examiner

FIG. 3
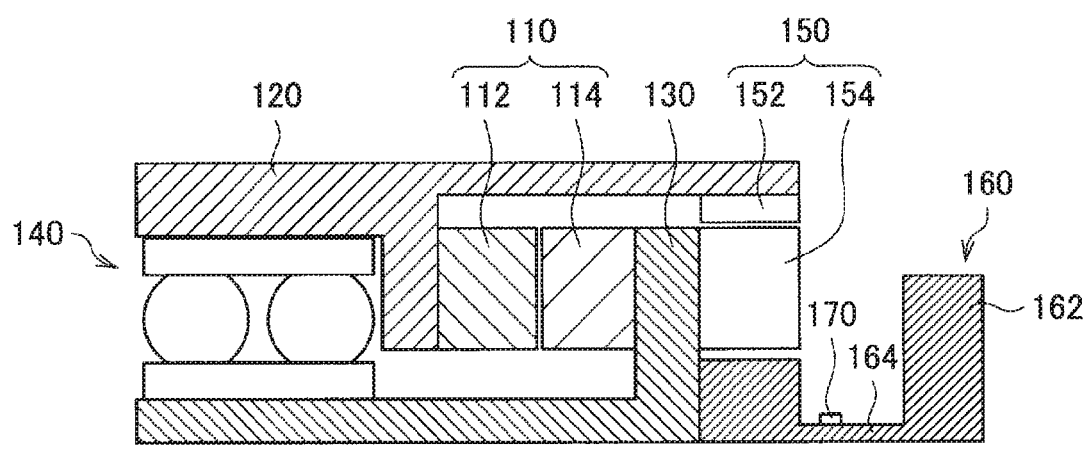
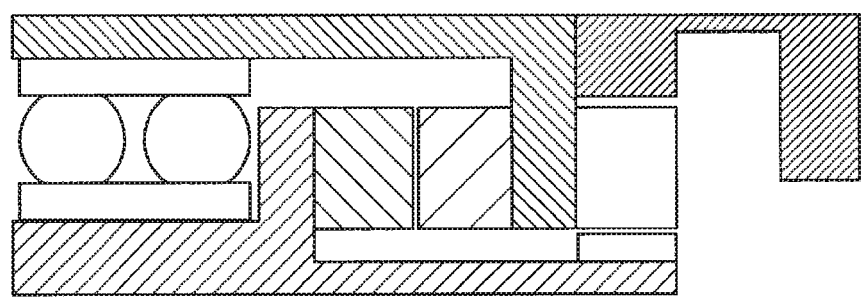

FIG. 4
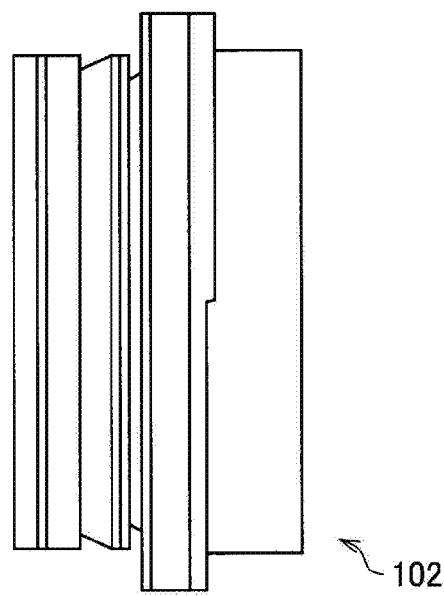
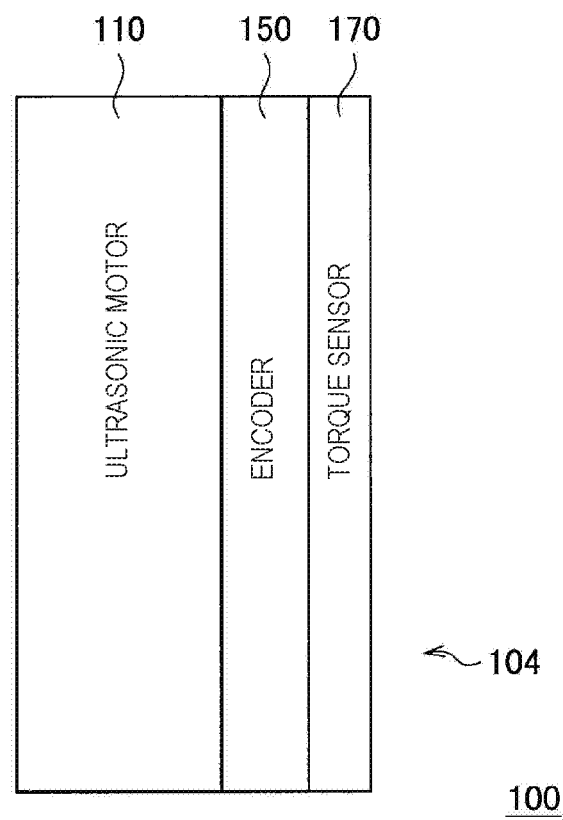

FIG. 5
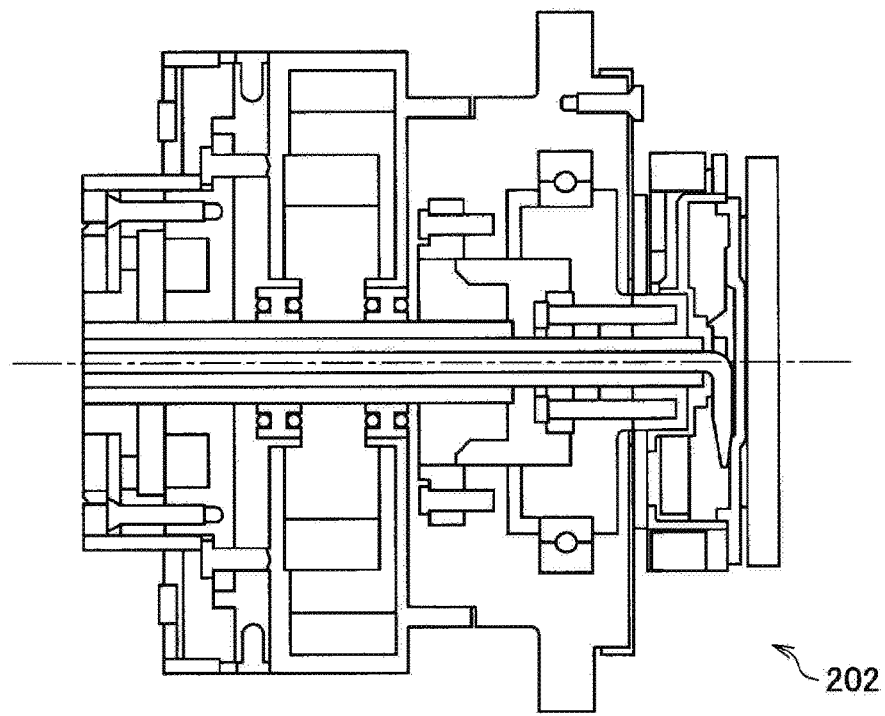
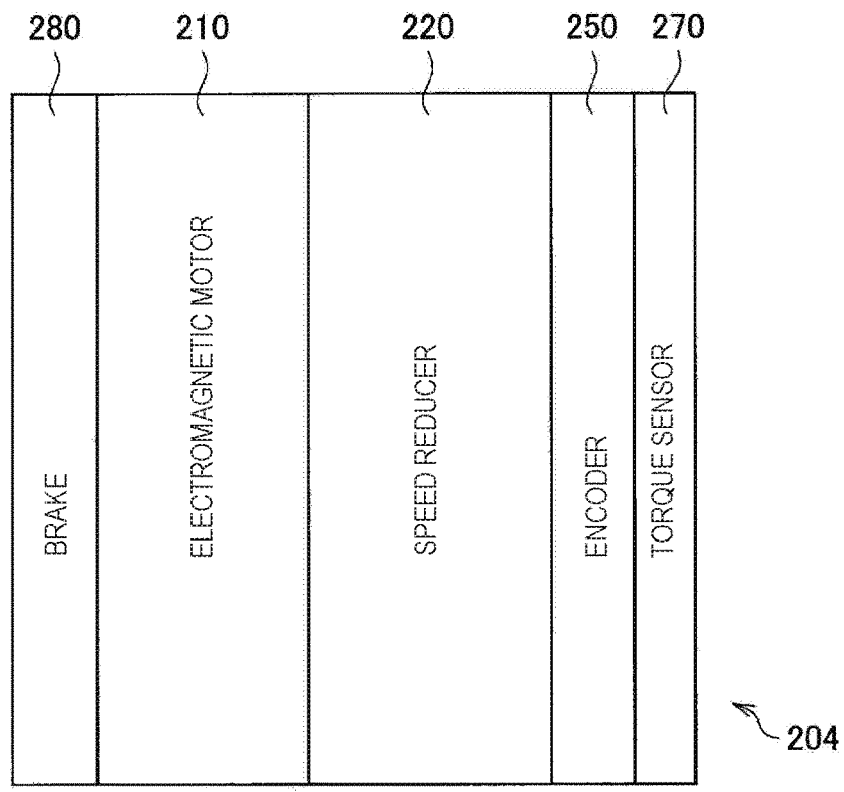

JOINT DRIVING ACTUATOR AND MEDICAL SYSTEM

CROSS-REFERENCE TO RELATED APPLICATIONS

The present application is based on PCT filing PCT/JP2017/037110, filed Oct. 13, 2017 which claims priority to JP 2016-219522, filed Nov. 10, 2016, the entire contents of which are incorporated herein by reference.

TECHNICAL FIELD

The present disclosure relates to a joint driving actuator and a medical system.

BACKGROUND ART

Conventionally, for example, Patent Literature 1 below describes an actuator that can suitably control driving of a joint actuator by a force control method that directly controls joint forming force.

CITATION LIST

Patent Literature

Patent Literature 1: JP 4715863B

DISCLOSURE OF INVENTION

Technical Problem

The actuator as described in Patent Literature 1 includes a torque sensor, an encoder, a speed reducer, an electromagnetic motor, a motor driver, and a microcomputer for control. In addition to this, to take measures against an arm drop during power loss, a brake is further added to the actuator. Therefore, a brake needs to be further added to the above configuration, which brings about a problem in that the configuration becomes complicated and larger.

Hence, it has been required that a joint driving actuator having a function of a brake be configured more simply.

Solution to Problem

According to the present disclosure, there is provided a joint driving actuator including: an ultrasonic motor configured to generate driving force for driving a joint; a torque sensor configured to detect external force applied to the joint; and an encoder configured to detect a rotational angle of the ultrasonic motor.

In addition, according to the present disclosure, there is provided a medical system including: a multi-joint arm that includes a plurality of joint portions and a plurality of links configured to rotatably connect the plurality of joint portions, and is configured to be able to support, at a distal end, an imaging apparatus configured to observe a surgical region; and a control system configured to control the multi-joint arm to change a position and a posture of the imaging apparatus with respect to the surgical region. At least one of the plurality of joint portions includes an ultrasonic motor configured to generate driving force for driving a joint, a torque sensor configured to detect external force applied to the joint, and an encoder configured to detect a rotational angle of the ultrasonic motor.

Advantageous Effects of Invention

According to the present disclosure as described above, a joint driving actuator having a function of a brake can be configured more simply.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3 is a cross-sectional diagram illustrating a configuration example of an actuator according to the present embodiment.

FIG. 4 schematically illustrates an exterior of the actuator according to the present embodiment, and a schematic configuration of the actuator.

FIG. 5 schematically illustrates a cross section of an actuator described in Patent Literature and a schematic configuration of the actuator.

MODE(S) FOR CARRYING OUT THE INVENTION

Figure 1:
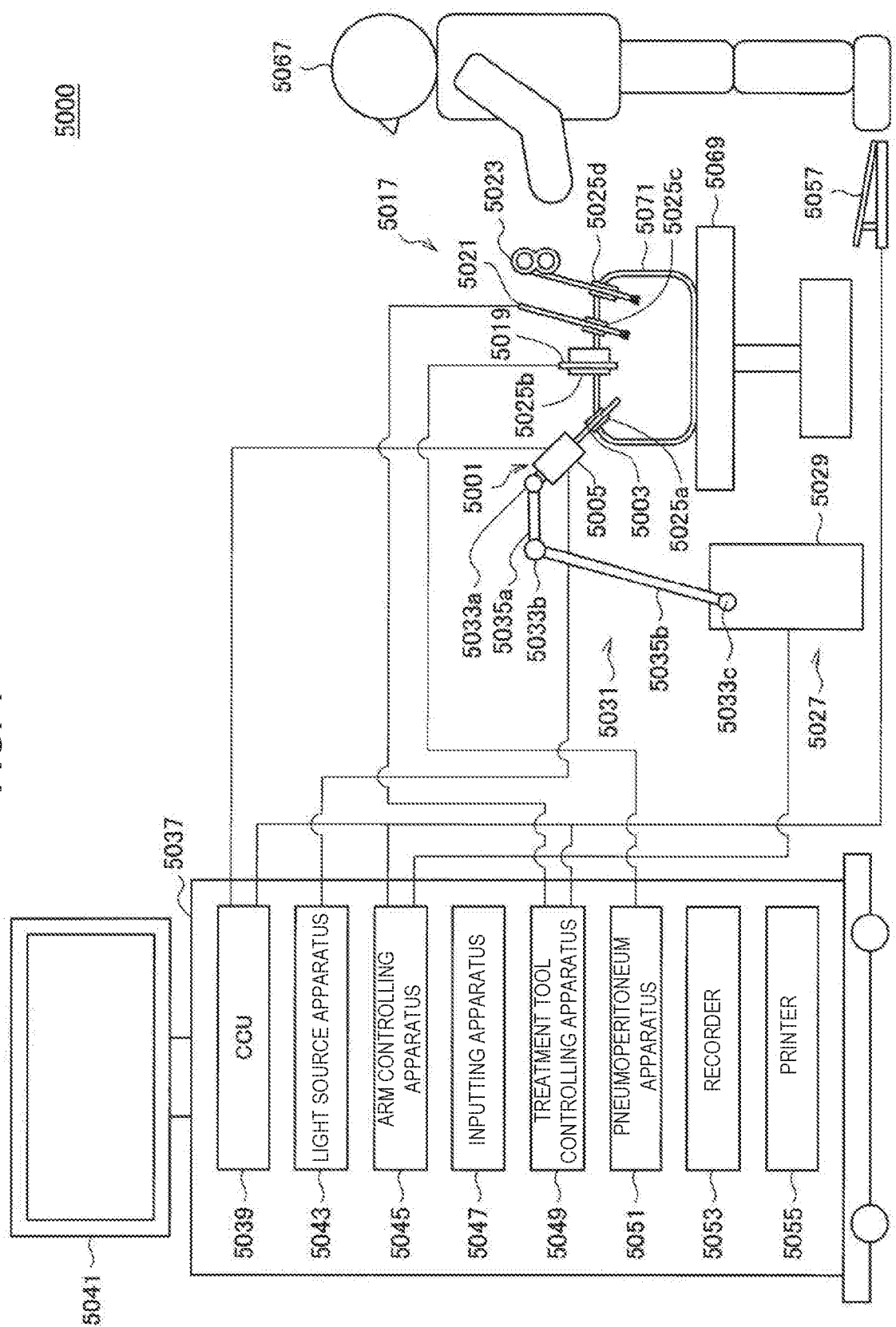
FIG. 1 is a view depicting an example of a schematic configuration of an endoscopic surgery system to which technology according to the present disclosure can be applied.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be given in the following order.
1. Configuration example of endoscopic system
2. Configuration example of actuator according to present embodiment
3. Application example

1. Configuration Example of Endoscopic System

FIG. 1 is a view depicting an example of a schematic configuration of an endoscopic surgery system 5000 to which the technology according to an embodiment of the present disclosure can be applied. In FIG. 1, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body cavity of the patient 5071 through the trocars 5025a to 5025d. In the example depicted, as the other surgical tools 5017, a pneumoperitoneum tube 5019, an energy device 5021 and forceps 5023 are inserted into body cavity of the patient 5071. Further, the energy device 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, tweezers or a retractor may be used.

An image of a surgical region in a body cavity of the patient 5071 imaged by the endoscope 5001 is displayed on a display apparatus 5041. The surgeon 5067 would use the energy device 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy device 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body cavity of the patient 5071, and a camera head 5005 connected to a proximal end of the lens barrel 5003. In the example depicted, the endoscope 5001 is depicted as a rigid endoscope having the lens barrel 5003 of the hard type. However, the endoscope 5001 may otherwise be configured as a flexible endoscope having the lens barrel 5003 of the flexible type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body cavity of the patient 5071 through the objective lens. It is to be noted that the endoscope 5001 may be a forward-viewing endoscope or may be an oblique-viewing endoscope or a side-viewing endoscope.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process), The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy device 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone, By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy device 5021 for cautery or incision of a tissue, sealing of a blood vessel or the like. A pneumoperitoneum apparatus 5051 feeds gas into a body cavity of the patient 5071 through the pneumoperitoneum tube 5019 to inflate the body cavity in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033a, 5033b and 5033c and the plurality of links 5035a and 5035b connected to each other by the joint portion 5033b. In FIG. 1, for simplified illustration, the configuration of the arm unit 5031 is depicted in a simplified form. Actually, the shape, number and arrangement of the joint portions 5033a to 5033c and the links 5035a and 5035b and the direction and so forth of axes of rotation of the joint portions 5033a to 5033c can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body cavity of the patient 5071.

An actuator is provided in each of the joint portions 5033a to 5033c, and the joint portions 5033a to 5033c are configured such that they are rotatable around predetermined axes of rotation thereof by driving of the respective actuators. The driving of the actuators is controlled by the arm controlling apparatus 5045 to control the rotational angle of each of the joint portions 5033a to 5033c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the operating room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the and unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower wavelength band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrow-band light and/or excitation light suitable for special light observation as described above.

(Camera Head and CCU)

Figure 2:
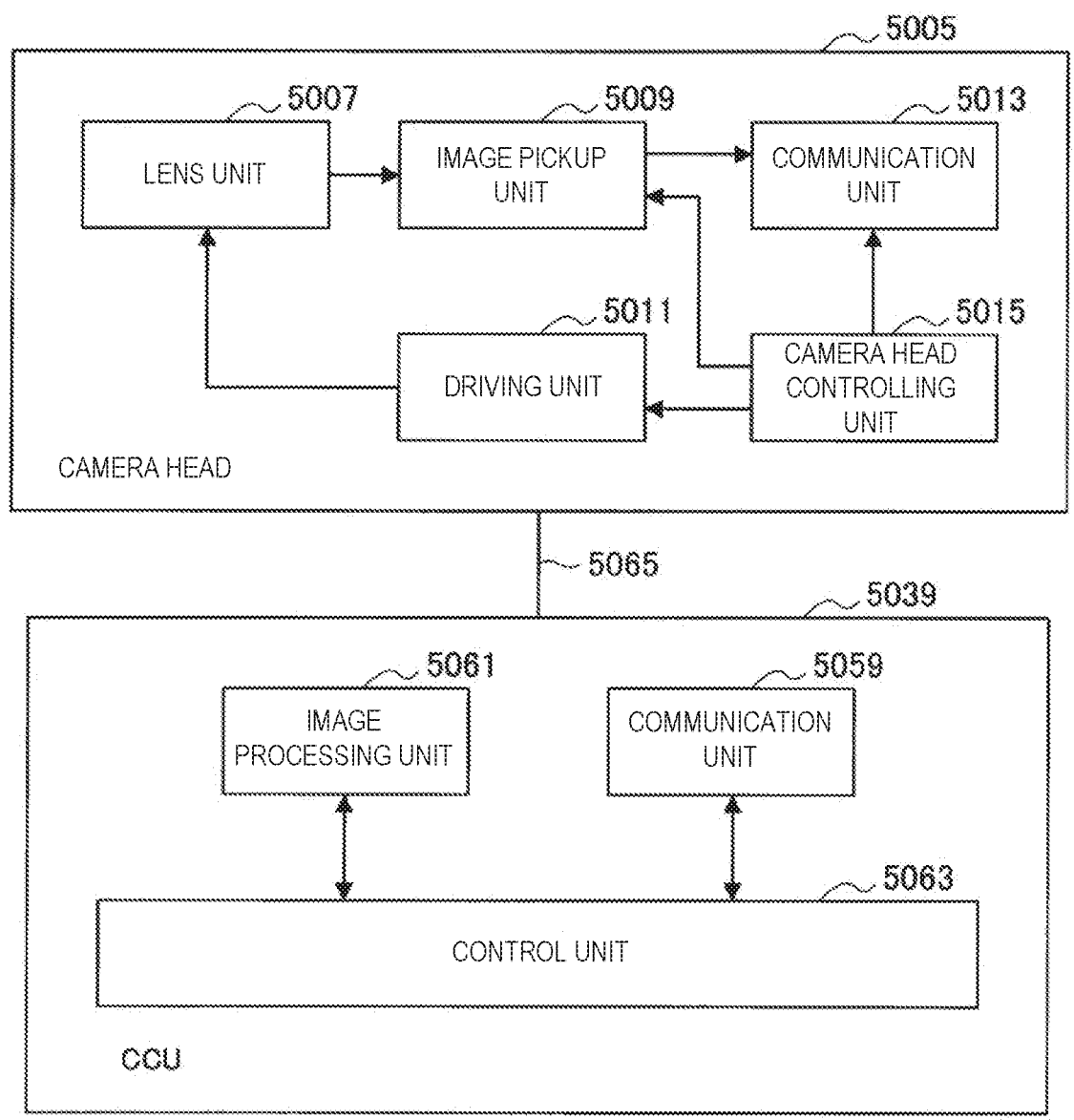
FIG. 2 is a block diagram depicting an example of a functional configuration of a camera head and a CCU depicted in FIG. 1.

Functions of the camera head 5005 of the endoscope 5001 and the CCU 5039 are described in more detail with reference to FIG. 2. FIG. 2 is a block diagram depicting an example of a functional configuration of the camera head 5005 and the CCU 5039 depicted in FIG. 1.

Referring to FIG. 2, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a band width enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy device 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the operating room. Therefore, such a situation that movement of medical staff in the operating room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a flexible endoscopic system for inspection or a microscopic surgery system.

2. Configuration Example of Actuator According to Present Embodiment

The technology according to the present disclosure can be suitably applied to actuators provided in the joint portions 5033a to 5033c, in the configuration of the endoscopic surgery system 5000 described above. FIG. 3 is a cross-sectional diagram illustrating a configuration example of an actuator 100 according to the present embodiment. The actuator 100 includes an ultrasonic motor 110, a fixed frame 120, a rotation frame 130, a bearing 140, an encoder 150, an output frame 160, and a torque sensor 170. The ultrasonic motor 110, the fixed frame 120, the rotation frame 130, the bearing 140, the encoder 150, and the output frame 160 all have a hollow ring shape.

The fixed frame 120 is fixed to one of two members that relatively rotate in the joint portions 5033a to 5033c. The ultrasonic motor 110 includes a stator 112 and a rotor 114. On the stator 112, a piezoelectric element (not illustrated) that venerates ultrasonic vibration is mounted. The rotor 114 is pressed against a vibration surface of the stator 112, and is rotated by ultrasonic vibration of the stator 112, The rotation frame 130 is fixed with respect to the rotor 114, and rotates together with the rotor 114. The bearing 140 is provided between the fixed frame 120 and the rotation frame 130, and is configured such that the rotation frame 130 rotates with respect to the fixed frame 120 through the bearing 140.

The output frame 160 is fixed with respect to the rotation frame 130, and rotates together with the rotation frame 130. An end portion 162 of the output frame 160 on the side opposite to the rotation frame 130 is fixed to the other of the two members that relatively rotate in the joint portions 5033a to 5033c. In addition, the output frame 160 is provided with a thin-walled portion 164 whose wall thickness in a radial direction is smaller than that of surroundings.

The torque sensor 170 is fixed to the thin-walled portion 164. The torque sensor 170 includes a strain gauge, and detects strain of the thin-walled portion 164 in the case where force is applied to the end portion 162 of the output frame 160, thereby detecting torque applied to the end portion 162.

As described above, the fixed frame 120 is fixed to one of two members that relatively rotate in the joint portions 5033a to 5033c, and the end portion 162 of the output frame 160 is fixed to the other of the two members that relatively rotate. For example, when the joint portion 5033b is taken as an example, the fixed frame 120 is fixed to the link 5035a side, and the end portion 162 of the output frame 160 is fixed to the link 5035b side. Thus, when the ultrasonic motor 110 is driven and the end portion 162 of the output frame 160 rotates with respect to the fixed frame 120, the link 5035a and the link 5035b are driven to relatively rotate. In addition, when a user applies external force to the arm unit 5031 to operate the arm unit 5031, the link 5035a and the link 5035b try to relatively rotate; thus, force of the end portion 162 of the output frame 160 trying to rotate with respect to the fixed frame 120 works. The torque sensor 170 detects the strain of the thin-walled portion 164 at this time, thereby detecting torque when the end portion 162 of the output frame 160 tries to rotate with respect to the fixed frame 120.

The encoder 150 includes a detector 152 and a rotor 154, and detects a rotational angle of the rotor 154 by the detector 152 detecting rotation of the rotor 154.

In the present embodiment, the arm controlling apparatus 5045 controls driving of the arm unit 5031 by force control. At this time, the arm controlling apparatus 5045 performs so-called power-assisted control to drive the actuators of the joint portions 5033a to 5033c such that the arm unit 5031 may receive external force by the user and move smoothly following the external force. At that time, external force from the user is detected by the torque sensor 170. In addition, by the encoder 150 detecting a rotational angle of the rotor 154 of each of the joint portions 5033a to 5033c, the posture of the arm unit 5031 can be comprehended, and external force corresponding to the posture is calculated by model calculation or the like in each of the joint portions 5033a to 5033c. In performing power-assisted control, it is desirable to drive the actuator by additionally considering external force corresponding to the posture. The arm controlling apparatus 5045 calculates driving force of the ultrasonic motor 110, on the basis of external force obtained from a detection value of the torque sensor 170 and external force corresponding to the posture obtained from model calculation or the like, and controls the ultrasonic motor 110 on the basis of the calculated driving force. Note that specific control can be performed by a technique similar to that of aforementioned Patent Literature 1. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

FIG. 4 schematically illustrates an exterior 102 of the actuator 100 according to the present embodiment, and a schematic configuration 104 of the actuator 100. In addition, FIG. 5 schematically illustrates a cross section 202 of an actuator 200 described in aforementioned Patent Literature 1, and a schematic configuration 204 of the actuator 200. As illustrated in FIG. 4, the actuator 100 of the present embodiment includes the ultrasonic motor 110, the encoder 150, and the torque sensor 170 as main structural elements.

In addition, as illustrated in FIG. 5, the actuator 200 described in aforementioned Patent Literature 1 includes an electromagnetic motor 210, a speed reducer 220 for increasing output of the electromagnetic motor 210, an encoder 250, and a torque sensor 270 as main structural elements.

When the actuator 100 according to the present embodiment and the actuator 200 described in Patent Literature 1 are compared on the basis of FIG. 4 and FIG. 5, functions of the encoder 250 and the torque sensor 270 of the actuator 200 are similar to functions of the encoder 150 and the torque sensor 170 of the actuator 100 of the present embodiment.

On the other hand, the actuator 200 uses the electromagnetic motor 210; since the electromagnetic motor 210 has high rotation speed and relatively small output torque, it is necessary to provide the speed reducer 220 to suppress rotation speed and increase output. On the other hand, since the actuator 100 uses the ultrasonic motor 110, the original motor rotation speed is relatively low, and a speed reducer need not be provided. Therefore, in the actuator 200, as compared with the actuator 100, providing the speed reducer 220 makes the structure complicated and also increases manufacturing cost.

Furthermore, since the electromagnetic motor 210 can rotate freely during power off, in the case where the actuator 200 is used, when power is lost by a power failure or the like, for example, the joint portions 5033a to 5033c of the arm unit 5031 become freely bendable, and there is a possibility that the arm unit 5031 drops down with gravity. Accordingly, as illustrated in FIG. 5, to take measures against an arm drop during power loss, the actuator 200 needs to have a brake 280. On the other hand, since the actuator 100 uses the ultrasonic motor 110, a brake is applied to the rotor 154 by the rotor 154 being pressed against the stator 112 during power off, during power loss, or the like. Accordingly, in the actuator 100 according to the present embodiment, a brake need not be additionally provided. Therefore, in the actuator 200, as compared with the actuator 100, providing the brake 280 makes the structure complicated and also increases manufacturing cost.

As described above, according to the actuator 100 according to the present embodiment, a structure can be made significantly simpler than that of the actuator 200. This enables a reduction in size of an apparatus and a significant reduction in manufacturing cost. Furthermore, the ultrasonic motor 110 has a hollow ring shape whose inner diameter is relatively large. In addition, parts such as the fixed frame 120, the rotation frame 130, the bearing 140, the encoder 150, and the output frame 160 also have a hollow ring shape like the ultrasonic motor 110. Accordingly, a wire harness or the like can be easily disposed in a hollow portion of the actuator 100, and routing of the harness in the arm unit 5031 can be performed easily.

In addition, according to the actuator 100 according to the present embodiment, using the ultrasonic motor 110 can make the structure simple; thus, the joint portions 5033a to 5033c can be significantly reduced in weight. Thus, inertial force in operating the arm unit 5031 decreases, and the arm unit 5031 can be operated more precisely. In addition, not using an electromagnetic motor prevents receiving magnetic influence, and in the case where a wire harness is disposed in the neighborhood of the joint portions 5033a to 5033c, magnetic influence on signals can be suppressed reliably.

Note that in the endoscopic surgery system 5000, the actuator 100 according to the present embodiment need not be provided in all of the joint portions 5033a to 5033c; the actuator 100 according to the present embodiment may be provided in part of the joint portions 5033a to 5033c, and the actuator 200 including the electromagnetic motor 210 may be provided in the rest of the joint portions 5033a to 5033c. Which of the actuator 100 and the actuator 200 is to be provided in each of the joint portions 5033a to 5033c can be decided as appropriate in accordance with specifications such as driving torque required of each of the joint portions 5033a to 5033c.

3. Application Example

The technology according to the present disclosure can be applied to a variety of products. For example, the technology according to the present disclosure may be applied to a microscopic surgery system used for so-called microsurgery that is performed while enlarging a minute region of a patient for observation.

Figure 6:
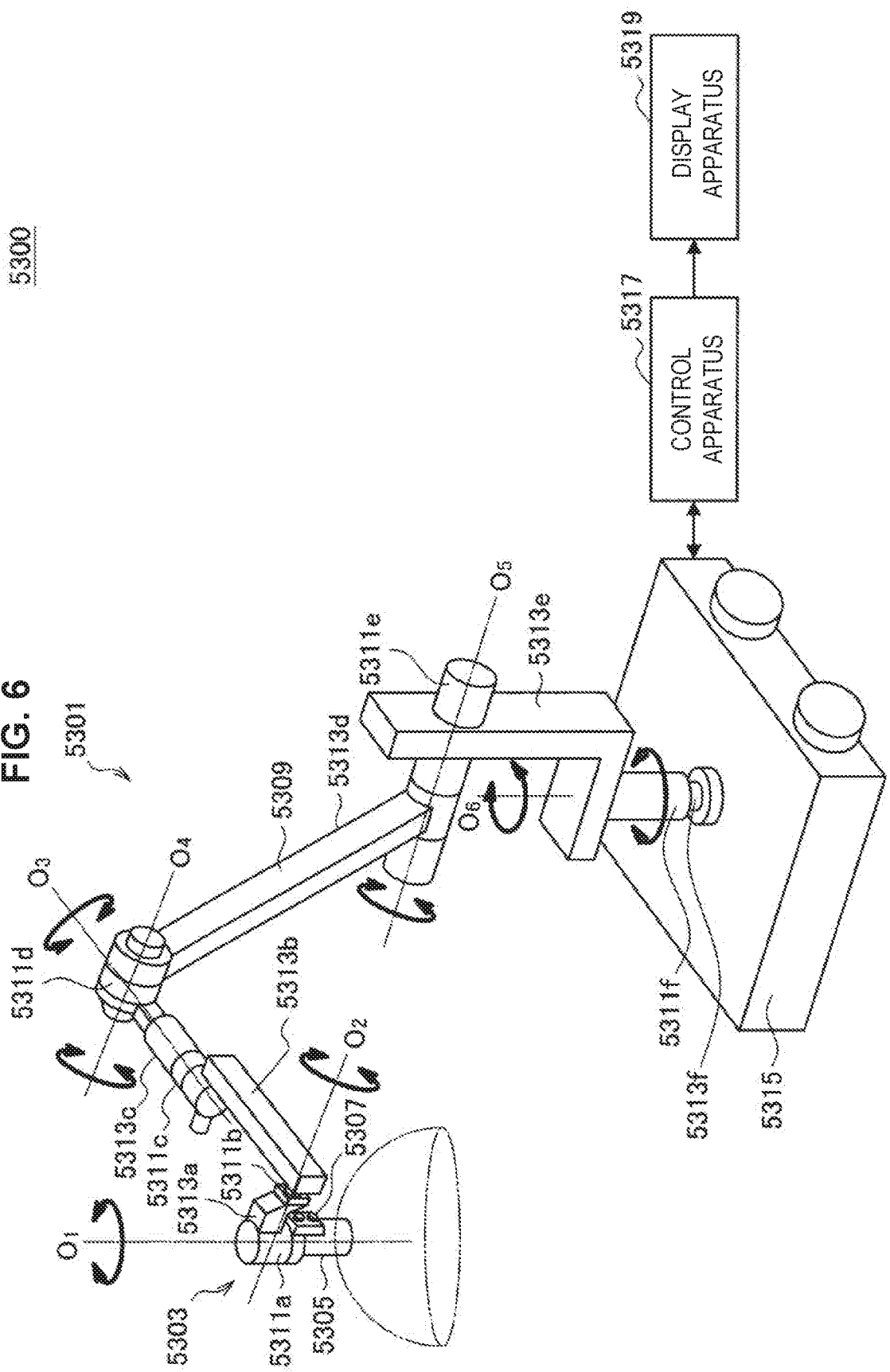
FIG. 6 is a view depicting an example of a schematic configuration of a microscopic surgery system to which technology according to the present disclosure can be applied.

FIG. 6 is a view depicting an example of a schematic configuration of a microscopic surgery system 5300 to which the technology according to an embodiment of the present disclosure can be applied. Referring to FIG. 6, the microscopic surgery system 5300 includes a microscope apparatus 5301, a control apparatus 5317 and a display apparatus 5319. It is to be noted that, in the description of the microscopic surgery system 5300, the term "user" signifies an arbitrary one of medical staff members such as a surgery or an assistant who uses the microscopic surgery system 5300.

The Microscope apparatus 5301 has a microscope unit 5303 for enlarging an observation target (surgical region of a patient) for observation, an arm unit 5309 which supports the microscope unit 5303 at a distal end thereof, and a base unit 5315 which supports a proximal end of the arm unit 5309.

The microscope unit 5303 includes a cylindrical portion 5305 of a substantially cylindrical shape, an image pickup unit (not depicted) provided in the inside of the cylindrical portion 5305, and an operation unit 5307 provided in a partial region of an outer circumference of the cylindrical portion 5305. The microscope unit 5303 is a microscope unit of the electronic image pickup type (microscope unit of the video type) which picks up an image electronically by the image pickup unit.

A cover glass member for protecting the internal image pickup unit is provided at an opening face of a lower end of the cylindrical portion 5305. Light from an observation target (hereinafter referred to also as observation light) passes through the cover glass member and enters the image pickup unit in the inside of the cylindrical portion 5305. It is to be noted that a light source includes, for example, a light emitting diode (LED) or the like may be provided in the inside of the cylindrical portion 5305, and upon image picking up, light may be irradiated upon an observation target from the light source through the cover glass member.

The image pickup unit includes an optical system which condenses observation light, and an image pickup element which receives the observation light condensed by the optical system. The optical system includes a combination of a plurality of lenses including a zoom lens and a focusing lens. The optical system has optical properties adjusted such that the observation light is condensed to be formed image on a light receiving face of the image pickup element. The image pickup element receives and photoelectrically converts the observation light to generate a signal corresponding to the observation light, namely, an image signal corresponding to an observation image. As the image pickup element, for example, an image pickup element which has a Bayer array and is capable of picking up an image in color is used. The image pickup element may be any of various known image pickup elements such as a complementary metal oxide semiconductor (CMOS) image sensor or a charge coupled device (CCD) image sensor. The image signal generated by the image pickup element is transmitted as RAW data to the control apparatus 5317. Here, the transmission of the image signal may be performed suitably by optical communication. This is because, since, at a surgery site, the surgeon performs surgery while observing the state of an affected area through a picked up image, in order to achieve surgery with a higher degree of safety and certainty, it is demanded for a moving image of the surgical region to be displayed on the real time basis as far as possible. Where optical communication is used to transmit the image signal, the picked up image can be displayed with low latency.

It is to be noted that the image pickup unit may have a driving mechanism for moving the zoom lens and the focusing lens of the optical system thereof along the optical axis. Where the zoom lens and the focusing lens are moved suitably by the driving mechanism, the magnification of the picked up image and the focal distance upon image picking up can be adjusted. Further, the image pickup unit may incorporate therein various functions which may be provided generally in a microscopic unit of the electronic image pickup such as an auto exposure (AE) function or an auto focus (AF) function.

Further the image pickup unit may be configured as an image pickup unit of the single-plate type which includes a single image pickup element or may be configured as an image pickup unit of the multi-plate type which includes a plurality of image pickup elements. Where the image pickup unit is configured as that of the multi-plate type, for example, image signals corresponding to red, green, and blue colors may be generated by the image pickup elements and may be synthesized to obtain a color image. Alternatively, the image pickup unit may be configured such that it has a pair of image pickup elements for acquiring image signals for the right eye and the left eye compatible with a stereoscopic vision (three dimensional (3D) display). Where 3D display is applied, the surgeon can comprehend the depth of a living body tissue in the surgical region with a higher degree of accuracy. It is to be noted that, if the image pickup unit is configured as that of stereoscopic type, then a plurality of optical systems are provided corresponding to the individual image pickup elements.

The operation unit 5307 includes, for example, a cross lever, a switch or the like and accepts an operation input of the user. For example, the user can input an instruction to change the magnification of the observation image and the focal distance to the observation target through the operation unit 5307. The magnification and the focal distance can be adjusted by the driving mechanism of the image pickup unit suitably moving the zoom lens and the focusing lens in accordance with the instruction. Further, for example, the user can input an instruction to switch the operation mode of the arm unit 5309 (an all-free mode and a fixed mode hereinafter described) through the operation unit 5307. It is to be noted that when the user intends to move the microscope unit 5303, it is supposed that the user moves the microscope unit 5303 in a state in which the user grasps the microscope unit 5303 holding the cylindrical portion 5305. Accordingly, the operation unit 5307 is preferably provided at a position at which it can be operated readily by the fingers of the user with the cylindrical portion 5305 held such that the operation unit 5307 can be operated even while the user is moving the cylindrical portion 5305.

The arm unit 5309 is configured such that a plurality of links (first link 5313a to sixth link 5313f) are connected for rotation relative to each other by a plurality of joint portions (first joint portion 5311a to sixth joint portion 5311f).

The first joint portion 5311a has a substantially columnar shape and supports, at a distal end (lower end) thereof, an upper end of the cylindrical portion 5305 of the microscope unit 5303 for rotation around an axis of rotation (first axis $O_1$) parallel to the center axis of the cylindrical portion 5305. Here, the first joint portion 5311a may be configured such that the first axis $O_1$ thereof is in alignment with the optical axis of the image pickup unit of the microscope unit 5303. By the configuration, if the microscope unit 5303 is rotated around the first axis $O_1$, then the field of view can be changed so as to rotate the picked up image.

The first link 5313a fixedly supports, at a distal end thereof, the first joint portion 5311a. Specifically, the first link 5313a is a bar-like member having a substantially L shape and is connected to the first joint portion 5311a such that one side at the distal end side thereof extends in a direction orthogonal to the first axis $O_1$ and an end portion of the one side abuts with an upper end portion of an outer periphery of the first joint portion 5311a. The second joint portion 5311b is connected to an end portion of the other side on the proximal end side of the substantially L shape of the first link 5313a.

The second joint portion 5311b has a substantially columnar shape and supports, at a distal end thereof, a proximal end of the first link 5313a for rotation around an axis of rotation (second axis $O_2$) orthogonal to the first axis $O_1$. The second link 5313b is fixedly connected at a distal end thereof to a proximal end of the second joint portion 5311b.

The second link 5313b is a bar-like member having a substantially L shape, and one side of a distal end side of the second link 5313b extends in a direction orthogonal to the second axis $O_2$ and an end portion of the one side is fixedly connected to a proximal end of the second joint portion 5311b. The third joint portion 5311c is connected to the other side at the proximal end side of the substantially L shape of the second link 5313b.

The third joint portion 5311c has a substantially columnar shape and supports, at a distal end thereof, a proximal end of the second link 5313b for rotation around an axis of rotation (third axis $O_3$) orthogonal to the first axis $O_1$ and the second axis $O_2$. The third link 5313c is fixedly connected at a distal end thereof to a proximal end of the third joint portion 5311c. By rotating the components at the distal end side including the microscope unit 5303 around the second axis $O_2$ and the third axis $O_3$, the microscope unit 5303 can be moved such that the position of the microscope unit 5303 is changed within a horizontal plane. In other words, by controlling the rotation around the second axis $O_2$ and the third axis $O_3$, the field of view of the picked up image can be moved within a plane.

The third link 5313c is configured such that the distal end side thereof has a substantially columnar shape, and a proximal end of the third joint portion 5311c is fixedly connected to the distal end of the columnar shape such that both of them have a substantially same center axis. The proximal end side of the third link 5313c has a prismatic shape, and the fourth joint portion 5311d is connected to an end portion of the third link 5313c.

The fourth joint portion 5311d has a substantially columnar shape and supports, at a distal end thereof, a proximal end of the third link 5313c for rotation around an axis of rotation (fourth axis $O_4$) orthogonal to the third axis $O_3$. The fourth link 5313d is fixedly connected at a distal end thereof to a proximal end of the fourth joint portion 5311d.

The fourth link 5313d is a bar-like member extending substantially linearly and is fixedly connected to the fourth joint portion 5311d such that it extends orthogonally to the fourth axis $O_4$ and abuts at an end portion of the distal end thereof with a side face of the substantially columnar shape of the fourth joint portion 5311d, The fifth joint portion 5311e is connected to a proximal end of the fourth link 5313d.

The fifth joint portion 5311e has a substantially columnar shape and supports, at a distal end side thereof, a proximal end of the fourth link 5313d for rotation around an axis of rotation (fifth axis $O_5$) parallel to the fourth axis $O_4$. The fifth link 5313e is fixedly connected at a distal end thereof to a proximal end of the fifth joint portion 5311e. The fourth axis $O_4$ and the fifth axis $O_5$ are axes of rotation around Which the microscope unit 5303 can be moved in the upward and downward direction. By rotating the components at the distal end side including the microscope unit 5303 around the fourth axis $O_4$ and the fifth axis $O_5$, the height of the microscope unit 5303, namely, the distance between the microscope unit 5303 and an observation target, can be adjusted.

The fifth link 5313e includes a combination of a first member having a substantially L shape one side of which extends in the vertical direction and the other side of which extends in the horizontal direction, and a bar-like second member extending vertically downwardly from the portion of the first member which extends in the horizontal direction. The fifth joint portion 5311e is fixedly connected at a proximal end thereof to a neighboring upper end of a part extending the first member of the fifth link 5313e in the vertical direction. The sixth joint portion 5311f is connected to proximal end (lower end) of the second member of the fifth link 5313e.

The sixth joint portion 5311f has a substantially columnar shape and supports, at a distal end side thereof, a proximal end of the fifth link 5313e for rotation around an axis of rotation (sixth axis $O_6$) parallel to the vertical direction. The sixth link 5313f is fixedly connected at a distal end thereof to a proximal end of the sixth joint portion 5311f.

The sixth link 5313f is a bar-like member extending in the vertical direction and is fixedly connected at a proximal end thereof to an upper face of the base unit 5315.

The first joint portion 5311a to sixth joint portion 5311f have movable ranges suitably set such that the microscope unit 5303 can make a desired movement. Consequently, in the arm unit 5309 having the configuration described above, a movement of totaling six degrees of freedom including three degrees of freedom for translation and three degrees of freedom for rotation can be implemented with regard to a movement of the microscope unit 5303. By configuring the arm unit 5309 such that six degrees of freedom are implemented for movements of the microscope unit 5303 in this manner, the position and the posture of the microscope unit 5303 can be controlled freely within the movable range of the arm unit 5309. Accordingly, it is possible to observe a surgical region from every angle, and surgery can be executed more smoothly.

It is to be noted that the configuration of the arm unit 5309 as depicted is an example at all, and the number and shape (length) of the links including the arm unit 5309 and the number, location, direction of the axis of rotation and so forth of the joint portions may be designed suitably such that desired degrees of freedom can be implemented. For example, in order to freely move the microscope unit 5303, preferably the arm unit 5309 is configured so as to have six degrees of freedom as described above. However, the arm unit 5309 may also be configured so as to have much greater degree of freedom (namely, redundant degree of freedom). Where a redundant degree of freedom exists, it is possible to change the posture of the arm unit 5309 in a state in which the position and the posture of the microscope unit 5303 are fixed. Accordingly, control can be implemented which is higher in convenience to the surgeon such as to control the posture of the arm unit 5309 such that, for example, the arm unit 5309 does not interfere with the field of view of the surgeon who watches the display apparatus 5319.

Here, an actuator in which a driving mechanism such as a motor, an encoder which detects an angle of rotation at each joint portion and so forth are incorporated may be provided for each of the first joint portion 5311a to sixth joint portion 5311f. By suitably controlling driving of the actuators provided in the first joint portion 5311a to sixth joint portion 5311f by the control apparatus 5317, the posture of the arm unit 5309, namely, the position and the posture of the microscope unit 5303, can be controlled. Specifically, the control apparatus 5317 can comprehend the posture of the arm unit 5309 at present and the position and the posture of the microscope unit 5303 at present on the basis of information regarding the angle of rotation of the joint portions detected by the encoders. The control apparatus 5317 uses the comprehended information to calculate a control value (for example, an angle of rotation or torque to be generated) for each joint portion with which a movement of the microscope unit 5303 in accordance with an operation input from the user is implemented. Accordingly, the control apparatus 5317 drives the driving mechanism of each joint portion in accordance with the control value. It is to be noted that, in this case, the control method of the arm unit 5309 by the control apparatus 5317 is not limited, and various known control methods such as force control or position control may be applied.

For example, when the surgeon performs operation inputting suitably through an inputting apparatus not depicted, driving of the arm unit 5309 may be controlled suitably in response to the operation input by the control apparatus 5317 to control the position and the posture of the microscope unit 5303. By this control, it is possible to support, after the microscope unit 5303 is moved from an arbitrary position to a different arbitrary position, the microscope unit 5303 fixedly at the position after the movement. It is to be noted that, as the inputting apparatus, preferably an inputting apparatus is applied which can be operated by the surgeon even if the surgeon has a surgical tool in its hand such as, for example, a foot switch taking the convenience to the surgeon into consideration. Further, operation inputting may be performed in a contactless fashion on the basis of gesture detection or line-of-sight detection in which a wearable device or a camera which is provided in the operating room is used. This makes it possible even for a user who belongs to a clean area to operate an apparatus belonging to an unclean area with a high degree of freedom. In addition, the arm unit 5309 may be operated in a master-slave fashion. In this case, the arm unit 5309 may be remotely controlled by the user through an inputting apparatus which is placed at a place remote from the operating room.

Further, where force control is applied, the control apparatus 5317 may perform power-assisted control to drive the actuators of the first joint portion 5311a to sixth joint portion 5311f such that the arm unit 5309 may receive external force by the user and move smoothly following the external force. This makes it possible to move, when the user holds and directly moves the position of the microscope unit 5303, the microscope unit 5303 with comparatively weak force. Accordingly, it becomes possible for the user to move the microscope unit 5303 more intuitively by a simpler and easier operation, and the convenience to the user can be improved.

Further, driving of the aria unit 5309 may be controlled such that the arm unit 5309 performs a pivot movement. The pivot movement here is a motion for moving the microscope unit 5303 such that the direction of the optical axis of the microscope unit 5303 is kept toward a predetermined point (hereinafter referred to as pivot point) in a space. Since the pivot movement makes it possible to observe the same observation position from various directions, more detailed observation of an affected area becomes possible. It is to be noted that, where the microscope unit 5303 is configured such that the focal distance thereof is fixed, preferably the pivot movement is performed in a state in which the distance between the microscope unit 5303 and the pivot point is fixed. In this case, it is sufficient if the distance between the microscope unit 5303 and the pivot point is adjusted to a fixed focal distance of the microscope unit 5303 in advance. By the configuration just described, the microscope unit 5303 comes to move on a hemispherical plane (schematically depicted in FIG. 6) having a diameter corresponding to the focal distance centered at the pivot point, and even if the observation direction is changed, a clear picked up image can be obtained. On the other hand, where the microscope unit 5303 is configured such that the focal distance thereof is adjustable, the pivot movement may be performed in a state in which the distance between the microscope unit 5303 and the pivot point is variable. In this case, for example, the control apparatus 5317 may calculate the distance between the microscope unit 5303 and the pivot point on the basis of information regarding the angles of rotation of the joint portions detected by the encoders and automatically adjust the focal distance of the microscope unit 5303 on the basis of a result of the calculation. Alternatively, where the microscope unit 5303 includes an AF function, adjustment of the focal distance may be performed automatically by the AF function every time the changing in distance caused by the pivot movement between the microscope unit 5303 and the pivot point.

Further, each of the first joint portion 5311a to sixth joint portion 5311f may be provided with a brake for constraining the rotation of the first joint portion 5311a to sixth joint portion 5311f. Operation of the brake may be controlled by the control apparatus 5317. For example, if it is intended to fix the position and the posture of the microscope unit 5303, then the control apparatus 5317 renders the brakes of the joint portions operative. Consequently, even if the actuators are not driven, the posture of the arm unit 5309, namely, the position and posture of the microscope unit 5303, can be fixed, and therefore, the power consumption can be reduced. When it is intended to move the position and the posture of the microscope unit 5303, it is sufficient if the control apparatus 5317 releases the brakes of the joint portions and drives the actuators in accordance with a predetermined control method.

Such operation of the brakes may be performed in response to an operation input by the user through the operation unit 5307 described hereinabove. When the user intends to move the position and the posture of the microscope unit 5303, the user would operate the operation unit 5307 to release the brakes of the joint portions. Consequently, the operation mode of the arm unit 5309 changes to a mode in which rotation of the joint portions can be performed freely (all-free mode). On the other hand, if the user intends to fix the position and the posture of the microscope unit 5303, then the user would operate the operation unit 5307 to render the brakes of the joint portions operative. Consequently, the operation mode of the arm unit 5309 changes to a mode in which rotation of the joint portions is constrained (fixed mode).

The control apparatus 5317 integrally controls operation of the microscopic surgery system 5300 by controlling operation of the microscope apparatus 5301 and the display apparatus 5319. For example, the control apparatus 5317 renders the actuators of the first joint portion 5311a to sixth joint portion 5311f operative in accordance with a predetermined control method to control driving of the arm unit 5309. Further, for example, the control apparatus 5317 controls operation of the brakes of the first joint portion 5311a to sixth joint portion 5311f to change the operation mode of the arm unit 5309. Further, for example, the control apparatus 5317 performs various signal processes for an image signal acquired by the image pickup unit of the microscope unit 5303 of the microscope apparatus 5301 to generate image data for display and controls the display apparatus 5319 to display the generated image data. As the signal processes, various known signal processes such as, for example, a development process (demosaic process), an image quality improving process (a bandwidth enhancement process, a super-resolution process, a noise reduction (NR) process and/or an image stabilization process) and/or an enlargement process (namely, an electronic zooming process) may be performed.

It is to be noted that communication between the control apparatus 5317 and the microscope unit 5303 and communication between the control apparatus 5317 and the first joint portion 5311a to sixth joint portion 5311f may be wired communication or wireless communication. Where wired communication is applied, communication by an electric signal may be performed or optical communication may be performed. In this case, a cable for transmission used for wired communication may be configured as an electric signal cable, an optical fiber or a composite cable of them in response to an applied communication method. On the other hand, where wireless communication is applied, since there is no necessity to lay a transmission cable in the operating room, such a situation that movement of medical staff in the operating room is disturbed by a transmission cable can be eliminated.

The control apparatus 5317 may be a processor such as a central processing unit (CPU) or a graphics processing unit (GPU), or a microcomputer or a control board in which a processor and a storage element such as a memory are incorporated. The various functions described hereinabove can be implemented by the processor of the control apparatus 5317 operating in accordance with a predetermined program. It is to be noted that, in the example depicted, the control apparatus 5317 is provided as an apparatus separate from the microscope apparatus 5301. However, the control apparatus 5317 may be installed in the inside of the base unit 5315 of the microscope apparatus 5301 and configured integrally with the microscope apparatus 5301. The control apparatus 5317 may also include a plurality of apparatus. For example, microcomputers, control boards or the like may be disposed in the microscope unit 5303 and the first joint portion 5311a to sixth joint portion 5311f of the arm unit 5309 and connected for communication with each other to implement functions similar to those of the control apparatus 5317.

The display apparatus 5319 is provided in the operating room and displays an image corresponding to image data generated by the control apparatus 5317 under the control of the control apparatus 5317. In other words, an image of a surgical region picked up by the microscope unit 5303 is displayed on the display apparatus 5319. The display apparatus 5319 may display, in place of or in addition to an image of a surgical region, various kinds of information relating to the surgery such as physical information of a patient or information regarding a surgical procedure of the surgery. In this case, the display of the display apparatus 5319 may be switched suitably in response to an operation by the user. Alternatively, a plurality of such display apparatus 5319 may also be provided such that an image of a surgical region or various kinds of information relating to the surgery may individually be displayed on the plurality of display apparatus 5319. It is to be noted that, as the display apparatus 5319, various known display apparatus such as a liquid crystal display apparatus or an electro luminescence (EL) display apparatus may be applied.

Figure 7:
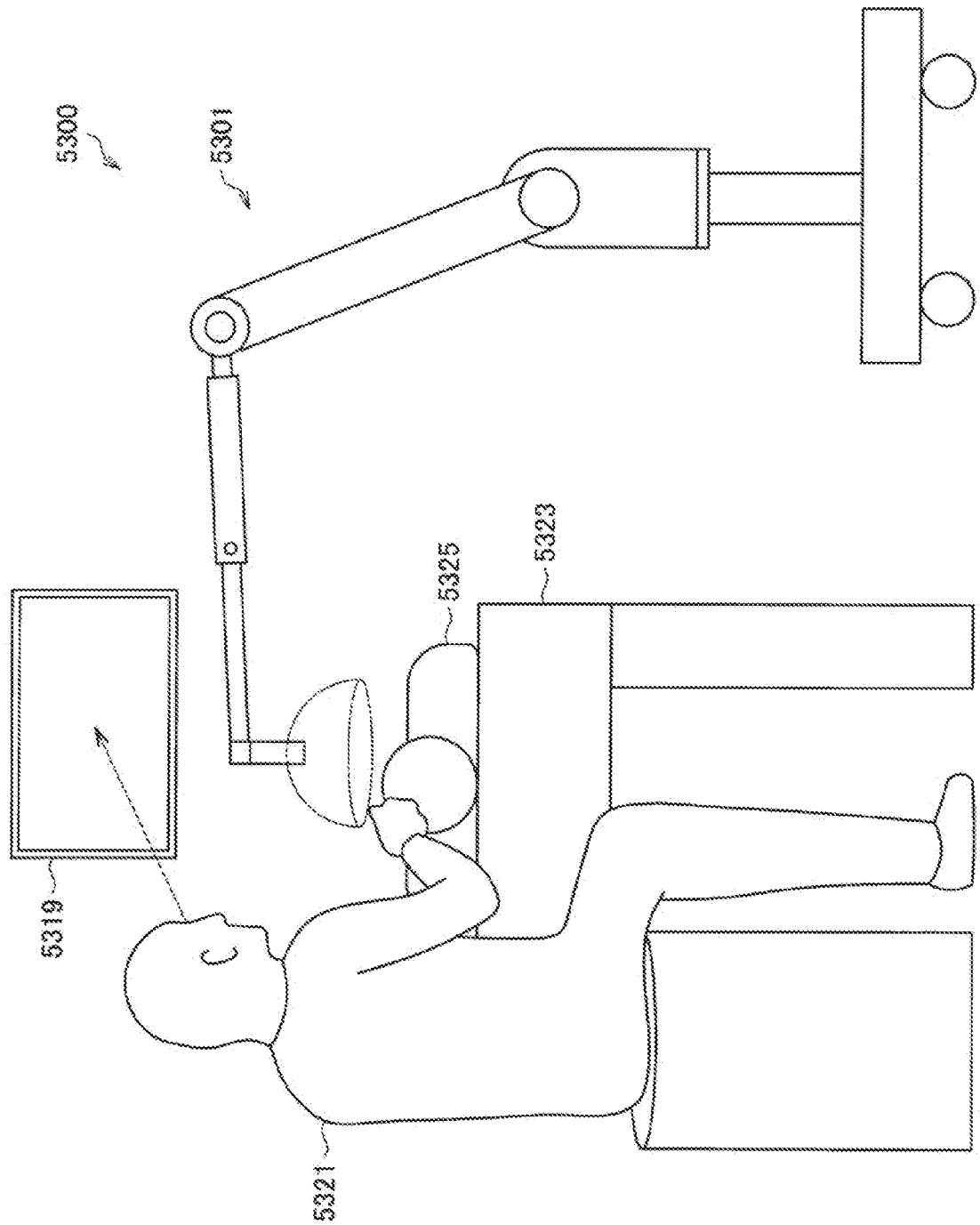
FIG. 7 is a view illustrating a state of surgery in which the microscopic surgery system depicted in FIG. 6 is used.

FIG. 7 is a view illustrating a state of surgery in which the microscopic surgery system 5300 depicted in FIG. 6 is used. FIG. 7 schematically illustrates a state in which a surgeon 5321 uses the microscopic surgery system 5300 to perform surgery for a patient 5325 on a patient bed 5323. It is to be noted that, in FIG. 7, for simplified illustration, the control apparatus 5317 from among the components of the microscopic surgery system 5300 is omitted and the microscope apparatus 5301 is depicted in a simplified from.

As depicted in FIG. 7, upon surgery, using the microscopic surgery system 5300, an image of a surgical region picked up by the microscope apparatus 5301 is displayed in an enlarged scale on the display apparatus 5319 installed on a wall face of the operating room. The display apparatus 5319 is installed at a position opposing to the surgeon 5321, and the surgeon 5321 would perform various treatments for the surgical region such as, for example, resection of the affected area while observing a state of the surgical region from a video displayed on the display apparatus 5319.

An example of the microscopic surgery system 5300 to which the technology according to an embodiment of the present disclosure can be applied has been described. It is to be noted here that, while the microscopic surgery system 5300 is described as an example, the system to which the technology according to an embodiment of the present disclosure can be applied is not limited to this example. For example, the microscope apparatus 5301 may also function as a supporting arm apparatus which supports, at a distal end thereof, a different observation apparatus or some other surgical tool in place of the microscope unit 5303. As the other observation apparatus, for example, an endoscope may be applied. Further, as the different surgical tool, forceps, tweezers, a pneumoperitoneum tube for pneumoperitoneum or an energy device for performing incision of a tissue or sealing of a blood vessel by cautery and so forth can be applied. By supporting any of such an observation apparatus and surgical tools as just described by the supporting apparatus, the position of them can be fixed with a high degree of stability in comparison with that in an alternative case in which they are supported by hands of medical staff. Accordingly, the burden on the medical staff can be reduced. The technology according to an embodiment of the present disclosure may be applied to a supporting arm apparatus which supports such a component as described above other than the microscopic unit.

The technology according to the present disclosure can be suitably applied to actuators of the first joint portion 5311*a* to sixth joint portion 5311*f* in the configuration described above.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally conic under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A joint driving actuator including:

an ultrasonic motor configured to generate driving force for driving a joint;

a torque sensor configured to detect external force applied to the joint; and an encoder configured to detect a rotational angle of the ultrasonic motor.

(2)

The joint driving actuator according to (1), in which the ultrasonic motor is driven on the basis of external force detected by the torque sensor.

(3)

The joint driving actuator according to (1) or (2), in which the ultrasonic motor is driven on the basis of a rotational angle detected by the encoder.

(4)

The joint driving actuator according to any one of (1) to (3), in which a stator of the ultrasonic motor is fixed to a side of one arm that relatively rotates in the joint, and a rotor of the ultrasonic motor is fixed to a side of another arm that relatively rotates in the joint.

(5)

The joint driving actuator according to (4), including a rotation member fixed to the rotor, in which the rotation member is fixed to the side of the other arm that relatively rotates in the joint.

(6)

The joint driving actuator according to (5), in which the torque sensor includes a strain gauge mounted on the rotation member.

(7)

The joint driving actuator according to any one of (1) to (6), in which the joint driving actuator is provided in the joint of a supporting arm configured to support a medical apparatus.

(8)

A medical system including:

a multi-joint arm that includes a plurality of joint portions and a plurality of links configured to rotatably connect the plurality of joint portions, and is configured to be able to support, at a distal end, an imaging apparatus configured to observe a surgical region; and a control system configured to control the multi joint arm to change a position and a posture of the imaging apparatus with respect to the surgical region, in which at least one of the plurality of joint portions includes an ultrasonic motor configured to generate driving force for driving a joint, a torque sensor configured to detect external force applied to the joint, and an encoder configured to detect a rotational angle of the ultrasonic motor.

(9)

The medical system according to (8), in which the imaging apparatus is a microscope.

(10)

The medical system according to (8), in which the imaging apparatus is an endoscope.

(11)

The medical system according to any one of (8) to (10), in which at least one of the plurality of joint portions includes an electromagnetic motor configured to generate driving force for driving a joint.

(12)

The medical system according to any one of (8) to (11), in which a harness is disposed in a hollow portion of the ultrasonic motor.

REFERENCE SIGNS LIST

100 actuator
110 ultrasonic motor 112 stator
114 rotor
150 encoder
170 torque sensor
5033a to 5033c joint portions
5309 arm unit
5317 control apparatus

The invention claimed is:

1. A joint driving actuator comprising:
an ultrasonic motor configured to generate driving force for driving a joint, the ultrasonic motor including a stator fixed to a side of one arm that relatively rotates in the joint and a rotor fixed to a side of another arm that relatively rotates in the joint, the stator including a piezoelectric element that generates ultrasonic vibration;
a torque sensor configured to detect external force applied to the joint; and
an encoder configured to detect a rotational angle of the ultrasonic motor, wherein
the encoder is mouthed on the one arm the stator being fixed on the side thereof, and
the torque sensor is mounted on the another arm, the rotor being fixed on the side thereof.

2. The joint driving actuator according to claim 1, wherein the ultrasonic motor is driven on a basis of the external force detected by the torque sensor.

3. The joint driving actuator according to claim 1, wherein the ultrasonic motor is driven on a basis of the rotational angle detected by the encoder.

4. The joint driving actuator according to claim 1, comprising
a rotation member fixed to the rotor, wherein
the rotation member is fixed to the side of the another arm.

5. The joint driving actuator according to claim 4, wherein the torque sensor includes a strain gauge mounted on the rotation member.

6. The joint driving actuator according to claim 1, wherein the joint driving actuator is provided in the joint of a supporting arm configured to support a medical apparatus.

7. The joint driving actuator according to claim 1, wherein the torque sensor is mounted on an end portion attached to the another arm, and
the torque sensor is mounted on the another arm via the end portion.

8. A medical system comprising:
a multi joint arm that includes a plurality of joint portions and a plurality of links configured to rotatably connect the plurality of joint portions, and is configured to be able to support, at a distal end, an imaging apparatus configured to observe a surgical region; and
a control system configured to control the multi joint arm to change a position and a posture of the imaging apparatus with respect to the surgical region, wherein
at least one of the plurality of joint portions includes
an ultrasonic motor configured to generate driving force for driving a joint, the ultrasonic motor including a stator fixed to a side of one arm that relatively rotates in the joint and a rotor fixed to a side of another arm that relatively rotates in the joint, the stator including a piezoelectric element that generates ultrasonic vibration,
a torque sensor configured to detect external force applied to the joint, and
an encoder configured to detect a rotational angle of the ultrasonic motor,
the encoder is mounted on the one arm, the stator being fixed on the side thereof, and
the torque sensor is mounted on the another arm, the rotor being fixed on the side thereof.

9. The medical system according to claim 8, wherein the imaging apparatus is a microscope.

10. The medical system according to claim 8, wherein the imaging apparatus is an endoscope.

11. The medical system according to claim 8, wherein at least one of the plurality of joint portions includes an electromagnetic motor configured to generate driving force for driving a joint of the plurality of joint portions.

12. The medical system according to claim 8, wherein a harness is disposed in a hollow portion of the ultrasonic motor.

* * * * *